United States Patent
Yoder et al.

(10) Patent No.: US 11,864,801 B2
(45) Date of Patent: Jan. 9, 2024

(54) IMPLANTABLE UNIVERSAL CONNECTOR

(71) Applicant: SeaSpine, Inc., Carlsbad, CA (US)

(72) Inventors: Zebulon Allen Yoder, Vista, CA (US); Tyler John Holschlag, Vista, CA (US); Christopher Marden John Cain, Denver, CO (US)

(73) Assignee: SeaSpine, Inc., Carlsbad, CA (US)

( * ) Notice: Subject to any disclaimer, the term of this patent is extended or adjusted under 35 U.S.C. 154(b) by 112 days.

(21) Appl. No.: 16/528,480

(22) Filed: Jul. 31, 2019

(65) Prior Publication Data
US 2021/0030448 A1  Feb. 4, 2021

(51) Int. Cl.
*A61B 17/70* (2006.01)
*A61B 17/56* (2006.01)

(52) U.S. Cl.
CPC ...... *A61B 17/7049* (2013.01); *A61B 17/7041* (2013.01); *A61B 2017/564* (2013.01)

(58) Field of Classification Search
CPC ............ A61B 17/7049; A61B 17/7041; A61B 2017/564; A61B 17/705; A61B 17/7052; A61B 17/7043; A61B 17/704
See application file for complete search history.

(56) References Cited

U.S. PATENT DOCUMENTS

| | | | |
|---|---|---|---|
| 5,486,174 A * | 1/1996 | Fournet-Fayard | A61B 17/7037 606/267 |
| 7,473,267 B2 | 1/2009 | Nguyen | |
| 7,833,251 B1 | 11/2010 | Ahlgren et al. | |
| 7,909,854 B2 * | 3/2011 | Schwab | A61B 17/705 606/250 |
| 8,313,515 B2 | 11/2012 | Brennan et al. | |
| 8,430,916 B1 * | 4/2013 | Winslow | A61B 17/7007 606/250 |
| 9,005,249 B2 | 4/2015 | Rinner et al. | |
| 9,539,028 B2 | 1/2017 | Dall et al. | |
| 10,383,663 B2 * | 8/2019 | Murray | A61B 17/7004 |
| 10,543,022 B2 * | 1/2020 | Italiaie | A61B 17/842 |
| 10,610,262 B2 * | 4/2020 | Castelein | A61B 17/7049 |
| 11,026,724 B2 * | 6/2021 | Ahn | A61B 17/7049 |
| 2005/0228378 A1 * | 10/2005 | Kalfas | A61B 17/705 606/252 |
| 2006/0058787 A1 | 3/2006 | David | |
| 2006/0241600 A1 | 10/2006 | Ensign et al. | |

(Continued)

FOREIGN PATENT DOCUMENTS

EP  1982663 A2 * 10/2008  ........... A61B 17/705
EP  1982663 A2   10/2008

(Continued)

OTHER PUBLICATIONS

Eom, et al. "Spinal fixation rod connector.", Jan. 6, 2017, Patent application (KR-20180081221-A) (English translation). (Year: 2017).*

(Continued)

*Primary Examiner* — Julianna N Harvey
(74) *Attorney, Agent, or Firm* — Dinsmore & Shohl LLP

(57) ABSTRACT

One or more connectors insertable into a surgical incision to couple rods together. The connector may include one or more bushings or joints to displace the one or more rods in one or more directions to a variety of orientations. One or more fasteners and/or bushings may be used to engage the one or more rods.

18 Claims, 9 Drawing Sheets

(56) References Cited

U.S. PATENT DOCUMENTS

| | | | |
|---|---|---|---|
| 2007/0161994 A1 | 7/2007 | Lowery et al. | |
| 2007/0282339 A1 | 12/2007 | Schwab | |
| 2009/0259256 A1* | 10/2009 | Miller | A61B 17/705 606/250 |
| 2014/0088650 A1 | 3/2014 | Taddia et al. | |
| 2015/0080953 A1 | 3/2015 | Otte et al. | |
| 2016/0166289 A1 | 6/2016 | Alsup et al. | |
| 2017/0128107 A1* | 5/2017 | Alsup | A61B 17/70 |
| 2018/0049773 A1 | 2/2018 | Backes | |
| 2018/0098798 A1 | 4/2018 | Italiaie et al. | |
| 2018/0228518 A1 | 8/2018 | Carruth et al. | |
| 2018/0280063 A1* | 10/2018 | Lee | A61B 17/705 |

FOREIGN PATENT DOCUMENTS

| | | | | |
|---|---|---|---|---|
| EP | 2277465 B1 | | 5/2015 | |
| EP | 3782566 | | 2/2021 | |
| KR | 20180081221 A | * | 7/2018 | |
| WO | 2005099603 A1 | | 10/2005 | |
| WO | WO-2018101633 A1 | * | 6/2018 | ......... A61B 17/7002 |

OTHER PUBLICATIONS

English-language translation of KR 2018-0081221; translated by the USPTO; Sep. 2021.*

English-language translation of WO 2018/101633; provided by EPO Patent Translate; accessed Jan. 12, 2023 (Year: 2023).*

European Patent Office, Communication and European Search Report for application No. 20189054.8 dated Jan. 27, 2021, 9 pages.

* cited by examiner

IMPLANTABLE UNIVERSAL CONNECTOR

FIELD

The present disclosure is directed to methods and apparatus for implantable connection of a rod or spinal implant to another spinal implant or rod.

BACKGROUND

Surgery, whether of the spine or other areas of the body, is often complex and routinely involves the need for highly experienced medical staff, in addition to well-designed and well-manufactured implants, made to exacting specifications. Often the implants take the form of various types of hardware. In the area of spinal fixation, for example, various spinal fixation devices have been developed in the art. Some examples of such fixation devices include spinal rods, plates, corpectomy cages, and intervertebral discs, to name but a few. Spinal fixation rods are fixation devices configured to fix adjacent vertebrae of a spine relative to each other. The rods provide stabilization of the spine till fusion occurs. The spinal fixation rods are often used in spinal surgeries to repair spinal abnormalities, whether related to injury or otherwise. The spinal rods are configured to attach to the vertebrae using, for example, anchoring devices like pedicle screws and hooks.

Patients often experience extreme and debilitating pain because of spinal column injuries or from spinal column disorders such as spondylolisthesis and scoliosis. Pain may be attributed to issues of the spine as related to degeneration, deformity, and/or injury. Often a typical course of treatment involves surgical spinal fixation utilizing spinal fixation rods that mechanically immobilize areas of the spine causing, ideally, the eventual fusion of the treated vertebrae.

Sometimes additional surgical procedures, known as revision surgeries, become necessary. Several causes exist for the need for revision surgeries. For example, pseudarthrosis (failure to achieve solid fusion) may have occurred, which can be due to various causes such as poor tissue healing, improper implant placement or securement, implant failure, or to patient-related factors. Sometimes revision surgeries are indicated even after successful initial surgeries, given that the function and shape of the spine can deteriorate with age. Also, after prolonged use, the spinal fixation rods may move or become dislodged or unstable, or even bend or break.

Revision surgery is also required to treat adjacent segment disease ("ASD"). Spinal fusion recipients may be at risk for developing ASD, a condition in which the motion segments adjacent to the fused vertebral segments experience higher rates of degeneration or deterioration due to an increase in vertebral loading, higher intradiscal pressures, increased range of motion, and increased facet motion. Treatment options for ASD begin with determining whether the primary fusion is intact. If so, then a revision surgery with a revision connector is a likely course of action.

What is needed is a universal revision connector that is easy to install, with minimal profile, and/or at desired angles with the primary fusion rod. The connector ideally minimizes the disruption of the previous fusion mass and imposes less violation of the scar tissue. The stabilization may be extended to the next level above or below the fusion. Additional benefit is also achieved with a connector that can be inserted percutaneously. Ideally, a connector is desired that is not only suitable for revision surgeries, but also for primary fusion surgeries. The present connector provides vast improvement over such existing revision connectors.

SUMMARY

In some embodiments of the invention, for example, an implantable connector system may comprise a connector having a first receptacle, a second receptacle, and a first bushing received in the first receptacle. In various embodiments, the connector may include a first threaded opening intersecting the first receptacle and a second threaded opening intersecting the second receptacle. In some embodiments, the system may include a first rod matingly received within the first bushing. In addition, in various embodiments, the system may include a second rod matingly received within the second receptacle. In some embodiments, the system may include a first fastener configured to threadably engage the first threaded opening. Moreover, in various embodiments, the system may include a second fastener configured to threadably engage the second threaded opening.

In some embodiments, the connector may further include a second bushing received within the second receptacle, and the second rod may be matingly received within the second bushing. In various embodiments, the second receptacle may include a slot extending through an outer periphery of the connector to receive the second rod. Moreover, in some embodiments, the first fastener and the second fastener may be a set screw. In various embodiments, the first receptacle of the connector may include a through hole and the first bushing may include an indentation, wherein the through hole of the first receptacle and the indentation of the first bushing may receive a portion of a pin. In some embodiments, the first bushing may be spherical and may include a slot. In various embodiments, the system may further include one or more pedicle screws.

In various embodiments, a connector for an implantable connector system may comprise a fixed body defining a first receptacle and a second receptacle. In some embodiments the first receptacle, the second receptacle, or both may have a bushing therein. In various embodiments, the connector may include a first threaded opening intersecting the first receptacle. Moreover, in some embodiments, the connector may include a second threaded opening intersecting the second receptacle. In various embodiments, the connector may include at least one first fastener threadingly engaging the first threaded opening and extending into said first receptacle of the body. In addition, in some embodiments, the connector may include at least one second fastener threadingly engaging the second threaded opening and extending into the second receptacle of the body.

In addition, in various embodiments, each one of the first receptacle and the second receptacle may include the bushing. In some embodiments, the second receptacle may include a slot extending through an outer periphery of the connector to receive a second rod. In various embodiments, the slot may pass through the second threaded opening. In some embodiments, the first receptacle of the connector may include a through hole and the bushing, wherein the bushing may include an indentation, and wherein the through hole of the first receptacle and the indentation of the bushing may receive a portion of a pin. Moreover, in various embodiments, the first receptacle may include a front opening connected to a back opening of an outer periphery of the fixed body. In some embodiments, the front opening may be a slot that the bushing passes through when being inserted into the first receptacle. In various embodiments, the bushing may allow displacement of a rod up to about 8 degrees about an axis of the first receptacle and/or the second receptacle, respectively.

Other embodiments may include a method of implanting an implantable connector system comprising the steps of providing a connector having a first receptacle, a second receptacle, and a first bushing positioned in the first receptacle. In some embodiments, the method may include inserting a first rod into the first bushing in the first receptacle. In various embodiments, the method may include inserting a second rod into the second receptacle. In addition, in some embodiments, the method may include threading a first fastener into engagement with the first bushing. In various embodiments, the method may include threading a second fastener into engagement with the second receptacle.

In addition, in some embodiments, the connector may include a second bushing in the second receptacle, and inserting the second rod into the second bushing in the second receptacle. In various embodiments, the method may include inserting the first bushing into the first receptacle and may include the first bushing being axially inserted into the first receptacle in a first orientation and pivoted to a second orientation different from the first orientation. In some embodiments, the method may include at least one of loading the second rod into the second receptacle by at least axially-loading, top-loading, or side-loading. Moreover, in various embodiments, the method may include displacing the first rod and the first bushing up to about 8 degrees from an axis of the first receptacle.

DESCRIPTION OF DRAWINGS

In the drawings, like reference characters generally refer to the same parts throughout the different views. Also, the drawings are not necessarily to scale, emphasis instead generally being placed upon illustrating the principles of the invention

DETAILED DESCRIPTION

The disclosure herein is directed to an apparatus, system, and method for use in primary or revision surgeries. The system or implantable connector system would typically include at least a connector, one or more fasteners, a rod, and one or more bushings in some embodiments.

Figure 1:
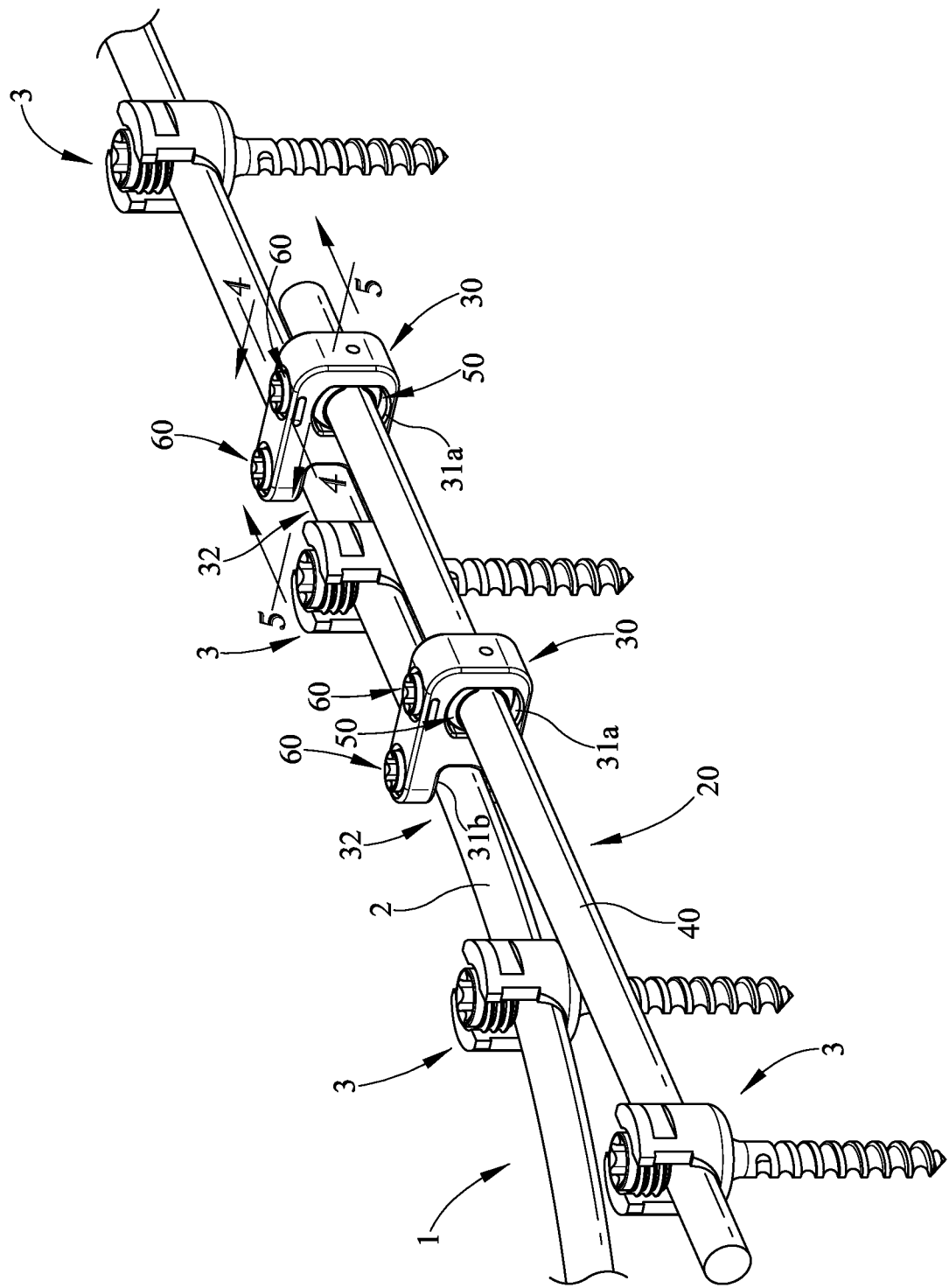
FIG. 1 is a perspective view of an embodiment of a system.

FIG. 1 shows a first embodiment of the implantable connector system 20 and/or connector 30. In the embodiments described herein, the context of a revision surgery will be used as an example, it being understood that the principles, methods, and structures involved are equally suited in the context of primary surgery as well. For example, in the context of a revision surgery, the embodiments describe the rod that is connected to the "primary fusion rod" to be a "revision rod". However, in primary fusion surgeries using the apparatus herein, the "revision rod" is more generically referred to as a secondary fusion rod.

In a first embodiment as shown in FIGS. 1-7, the apparatus includes a side-loading, connector 30 for coupling a revision rod 40, or secondary rod, to a primary (pre-existing, if in a revision surgery) fusion rod 2 of a pedicle screw system 1. The connector 30 is a laterally loaded configuration that fits over or cradles an existing rod 2 and spaces the rod 40 therefrom. One or more connectors 30 may be used to combine one or more rods, one or more pedicle screws, and/or other structure to the one or more pedicle screw systems or one or more rods. The connectors 30 may be coupled to one or more rods 2 that may be straight and/or curved (e.g. when rods are contoured to match the sagittal profile of the spine). The connectors 30 add on or extend existing fusion constructs or may increase the rigidity and corrective power and stability of a construct. Although the connector 30 may be laterally loaded as shown in the one embodiment (e.g. FIG. 1), the one or more connectors 130, 230 may be axially-loaded and/or top-loaded, respectively, with the rod 2 as well in some embodiments. Although the embodiment of the implantable connector system 20, as shown in FIG. 1, includes one or more pedicle screws 3 attached thereto, it should be understood that the system 20 may not include pedicle screws in some embodiments or applications.

Figure 5:
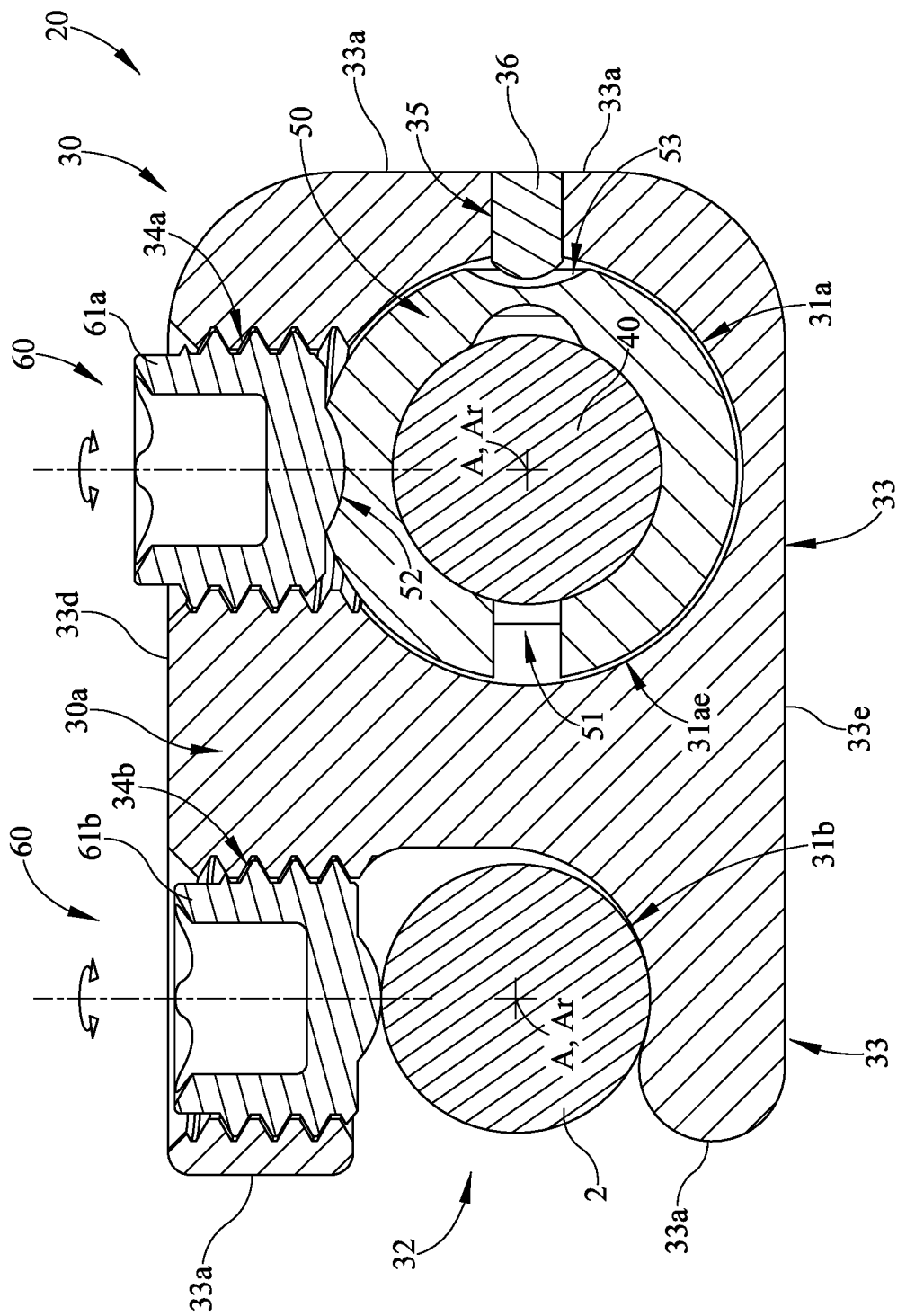
FIG. 5 is a sectional view taken along line 5-5 of FIG. 1.
Figure 8:
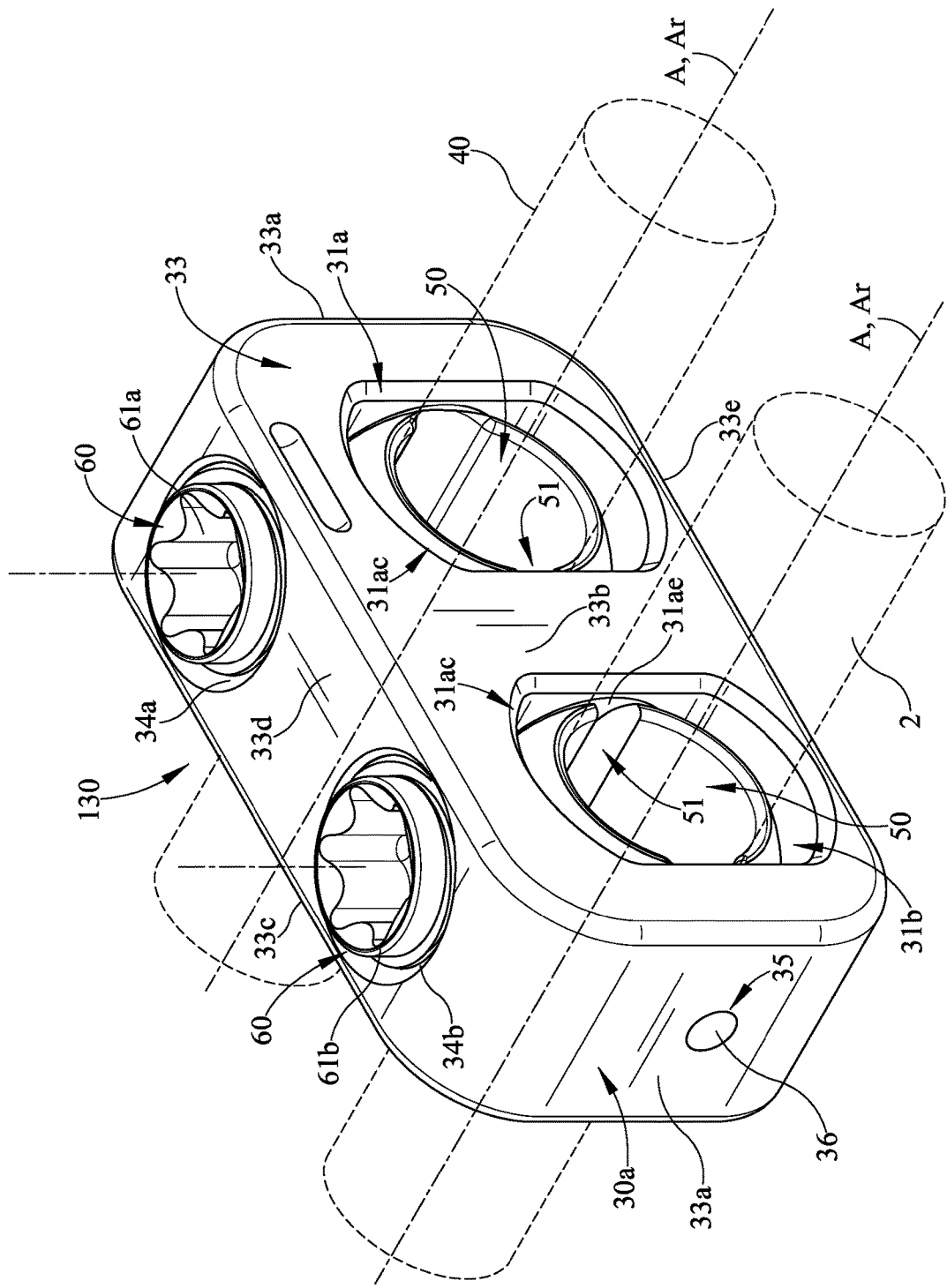
FIG. 8 is a top perspective view of another embodiment of a connector illustrating two bushings adapted to receive rods.

As shown in the embodiment of FIGS. 1-7, the connector 30 may include two or more receptacles 31a, 31b to couple or matingly receive the corresponding rods. This configuration may allow for connection to an existing construct wherein the connector may be placed between fixation points to the spine, pedicle screws or hooks, without having to remove the rod from these fixation points in order to place the connector. The connector 30 may include one or more bushings 50 positioned within the one or more receptacles. At least one of the receptacles or first receptacle 31a may include or receive the bushing 50. The bushing 50 may matingly receive the rod 40 (e.g. revision and/or primary rod). Spaced from and/or separate from the first receptacle 31a, is another or second receptacle(s) 31b. Although, the receptacles (e.g. first and second receptacles 31a, 31b) may be different from each other as shown in FIGS. 1-7, in some embodiments the receptacles may be similar (e.g. see FIG. 8). The second receptacle 31b may be aligned substantially parallel to the first receptacle 31a. Although not shown, the receptacles may not be parallel to each other in some embodiments. The second receptacle 31b may include a receiving slot 32 or be open to engage the primary fusion rod 2, pedicle screw 3, and/or portions of the pedicle screw system 1. The slot 32 may intersect the second receptacle/through opening 31b having an axis A. As shown in FIG. 5, the slot 32 receives the rod 2 (e.g. side-loading and/or laterally). The slot 32 may extend through an outer periphery 33 of the connector 30. The slot 32 may extend through a lateral side 33a or outer periphery 33 for a depth intersecting with a front side 33b and a back side 33c of the connector 30. The first receptacle 31a may be a through opening having an axis A. The through opening/first receptacle 31a may extend from the front side 33b to the back side 33c of the connector 30. The front side 33b includes a front opening 31ac and the back side 33c includes a back opening 31ad defining the through opening therebetween. The front opening 31ac and/or back opening 31ad of the through opening/ first receptacle 31a may be a slot or slot shaped. The slot shaped opening may receive (e.g. axially) the bushing 50 in one or more orientations, but not other orientations in some embodiments. The bushing 50 may be inserted into the front opening 31ac and/or back opening 31ad. The receptacles 31a, 31b may be a variety of shapes, sizes, quantities, positions, and constructions and still be within the scope of the invention.

In some implementations, the connector 30 may include or be defined as a fixed body 30a defining the receptacles 31a, 31b. The fastener 60 thereby reduces or impinges into the space defined by the receptacle/opening to engage the rod, bushing, and/or other structure within the receptacle.

In some implementations, the connector 30 may include one or more fasteners 60 securing the plurality of rods 2, 40 together for a variety of applications. These fasteners 60 may include at least a first fastener 61a and a second fastener 61b. The connector 30 may include one or more threaded openings 34a, 34b threadably receiving the corresponding fastener 61a, 61b. The one or more threaded openings 34a, 34b may intersect with the one or more receptacles 31a, 31b. The threaded opening 34a, 34b may intersect with the receptacle 31a, 31b to receive the fastener 60 and/or additional structure to secure the rod 2, 40, screw 3, and/or bushing 50. As shown in FIGS. 1-7, a first threaded opening 34a intersects the first receptacle 31a. The first threaded opening 34a may extend from a top side 33d of the connector 30 into the first receptacle 31a. As such, the fastener 60 (e.g. first fastener 61a) may compress or threadably engage the first threaded opening 34a and/or bushing 50, in a variety of orientations, within the first receptacle 31a to orient the received rods 40 desired orientation or application. The first fastener 61a may extend or project into the first receptacle 31a. The first fastener 61a may engage or compress the bushing 50 onto the rod 40. Further, a second threaded opening 34b intersects the second receptacle 31b. The second threaded opening 34b may extend from the top side 33d of the connector into the second receptacle 31b. As such, the second fastener 61b engages or compresses the primary rod 2 or threadably engages the second threaded opening 34b. The second fastener 61b may extend or project into the second receptacle 31b and/or bushing 50, if used in some embodiments. The first and second fastener 61a, 61b may engage their corresponding receptacle 31a, 31b, bushing 50, and/or rod independently/separately from the other.

The one or more fasteners 60 may be a variety of constructions, quantities, shapes and sizes and still be within the scope of the invention. As shown in the Figures, the one or more fasteners 60 may be a locking or set screw engaging the threadable opening and/or compressing/engaging the rod, bushing, and/or pedicel screw.

The one or more bushings 50 may be a variety of joints to orientate the one or more rods. In the one embodiment shown, the bushing 50 may be a universal ball joint to allow movement in a plurality of directions/planes. The bushing 50 may be spherical as shown. The bushing 50 may include a slot 51. The bushing 50 may include an indentation 52 proximal the top side 33d of the connector 30 to receive a portion of or a projection of the fastener 60 (e.g. set screw or first fastener 61a) to compress the bushing 50. When engaged, the fastener 60 may lock the orientation/angle θ of the rod/bushing. Further, in some embodiments, the bushing 50 may include a second indentation 53. The second indentation 53 may be opposite to the slot 51 of the bushing 50 and/or be located proximal the lateral side 33a of the connector 30. The second indentation 53 may align with a through hole 35 of the connector 30 extending to and intersecting the first receptacle 31a (e.g. through opening/ receptacle). The through hole 35 and the indentation 53 of the bushing 50 receives a portion of a pin 36 of the connector 30 to restrict at least some movement of the bushing 50 relative to the body 30a/receptacle 31a. For example, the pin 36 may reduce the removal of the bushing 50 from the first receptacle 31a. Moreover, the bushing 50 may be positioned in an annular groove 31ae within the first receptacle. As illustrated in FIG. 5, the through hole 35 may intersect the internal annular groove 31ae receiving the outer periphery of the bushing 50 when in the assembled position (see FIGS. 2 and 4). The inner periphery of the bushing may define a through opening to receive the rod. As such, the opening or slots 51, if used, may intersect with the through opening of the bushing. The bushing 50 may be a variety of shapes, sizes, quantities, positions, and constructions and still be within the scope of the invention.

Figure 6:
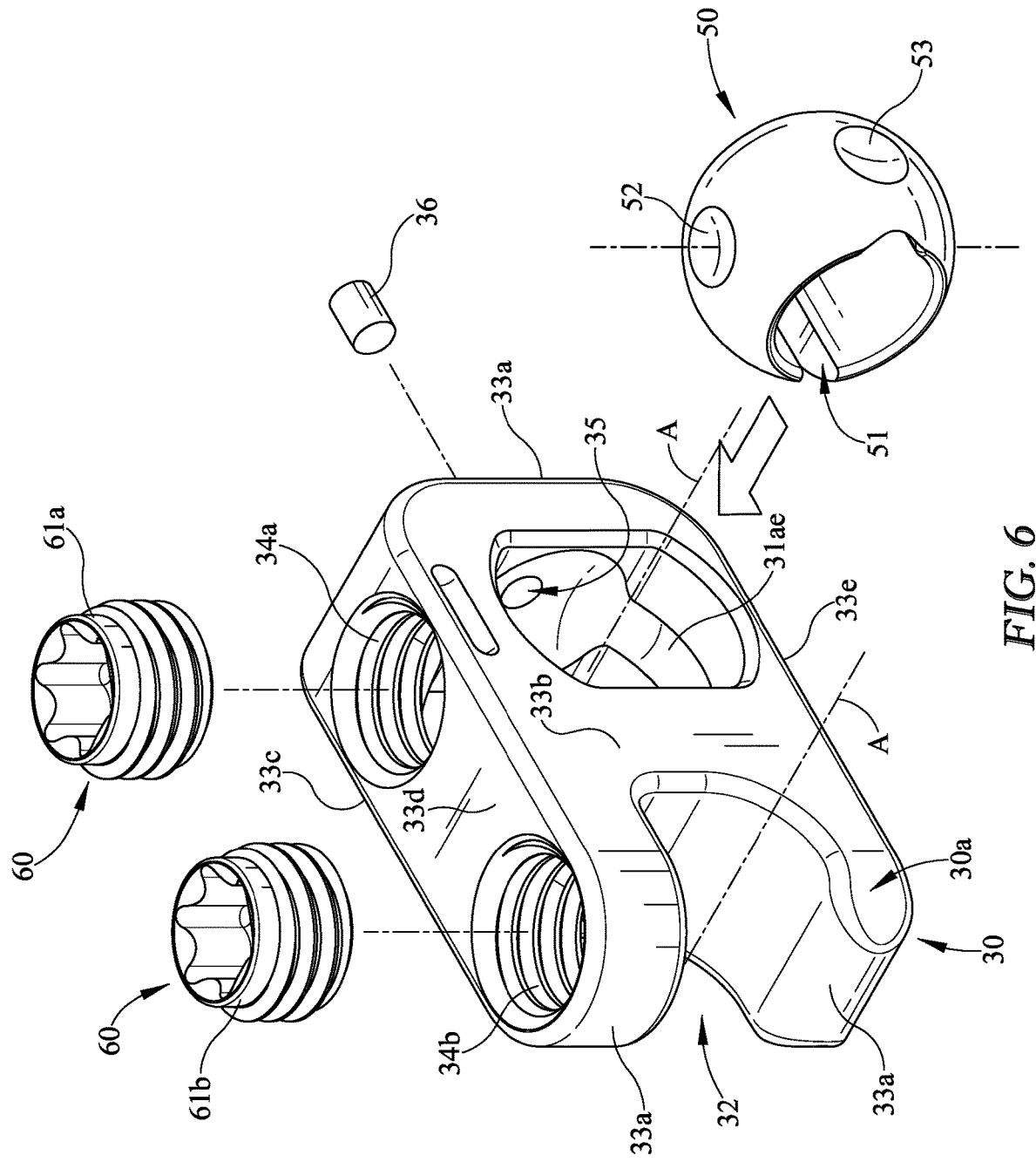
FIG. 6 is a top perspective view of the connector of FIG. 1 with the pin and fasteners exploded away therefrom, and illustrating the bushing in a first orientation different from a second orientation of the bushing in the assembled position.
Figure 7:
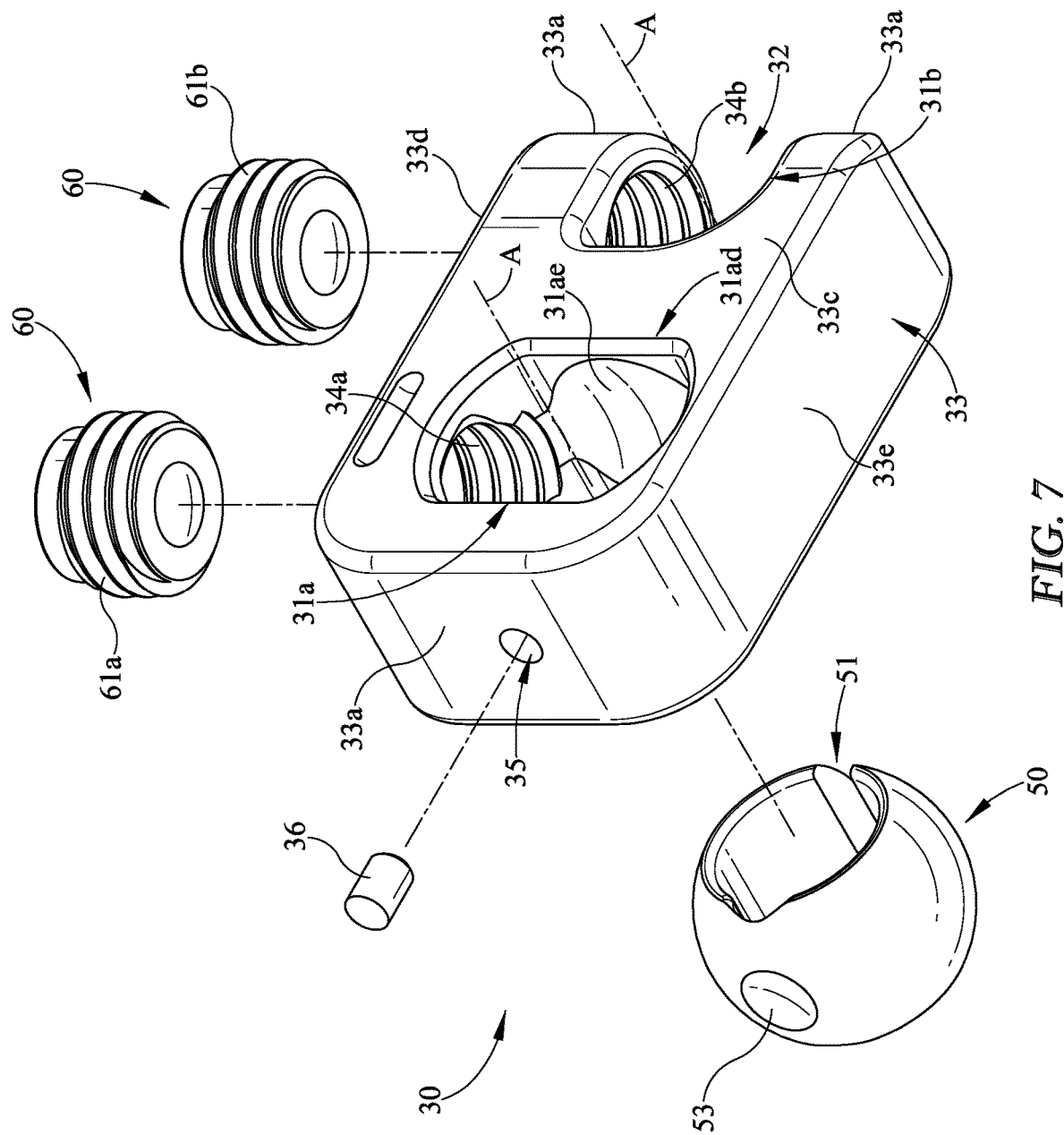
FIG. 7 is a bottom perspective view of the connector of FIG. 6 with the pin, fasteners, and bushing exploded away therefrom.

As illustrated in FIG. 6, the bushing 50 may be inserted into the first receptacle 31a/opening in an orientation different from the orientation of the bushing when in the assembled position (e.g. see FIG. 2) with the remaining portion of the connector. As shown in FIG. 6, the bushing 50 may include a first orientation to be inserted into the front and/or back opening 31ac, 31ad (e.g. slot) of the first receptacle 31a. The first orientation may be substantially parallel to the direction of the axis A of the through opening of the first receptacle. Once inserted into the through opening or slot of the front/back opening and positioned proximate the annular groove 31ae, if used, the bushing may be pivoted (e.g. about 90 degrees) such that bushing is aligned/ parallel to the annular groove or transverse to an axis A of the through opening/receptacle. Once pivoted to the second orientation or in the final assembled position within groove 31ae, the pin 36, if used, may be inserted into the through hole 35 and subsequently the indentation 53 of the outer periphery of the bushing.

Figure 2:
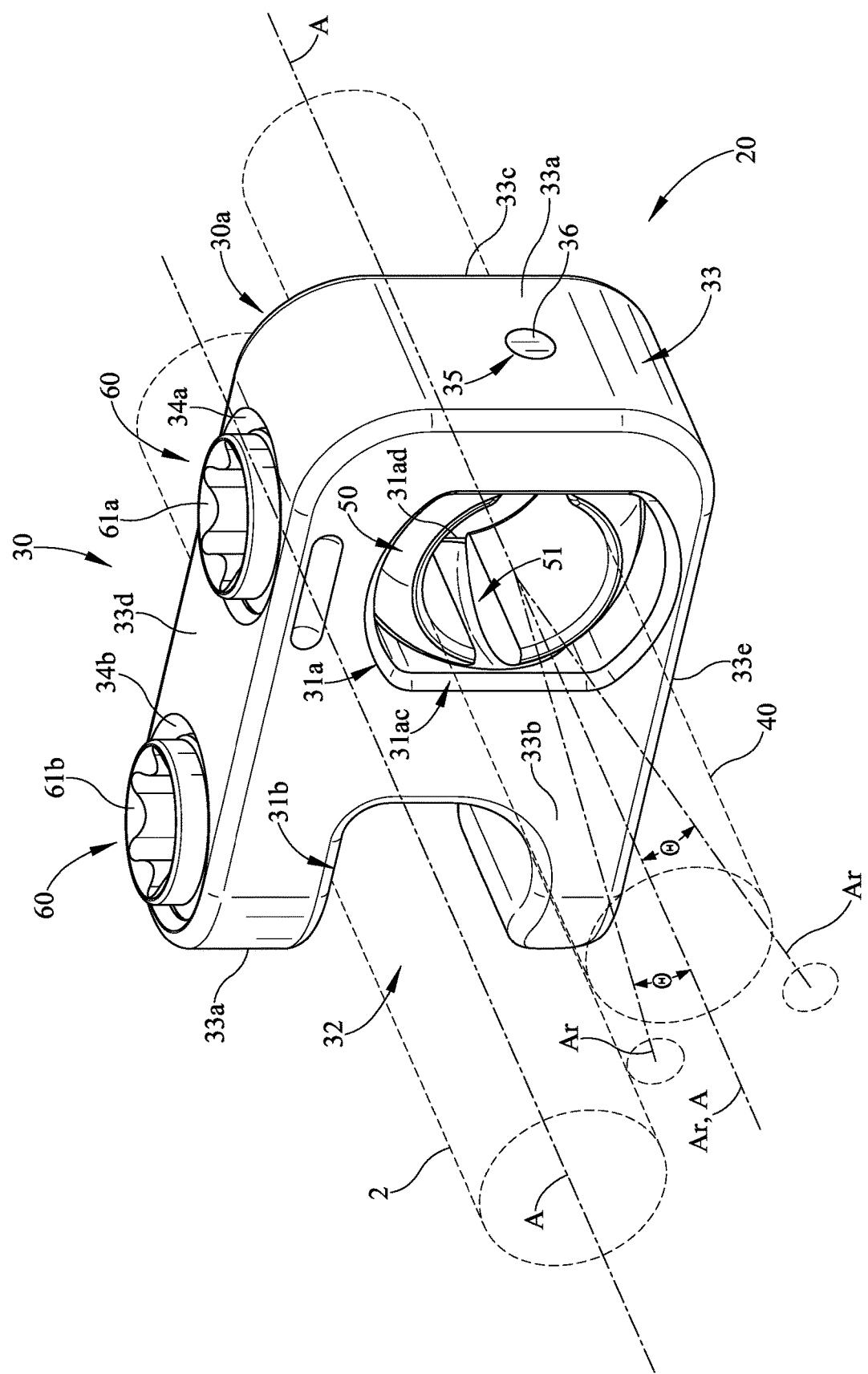
FIG. 2 is a top perspective view of the connector of FIG. 1 illustrating displacement of the rod within a first receptacle having a bushing and a lateral-loading second receptacle.
Figure 3:
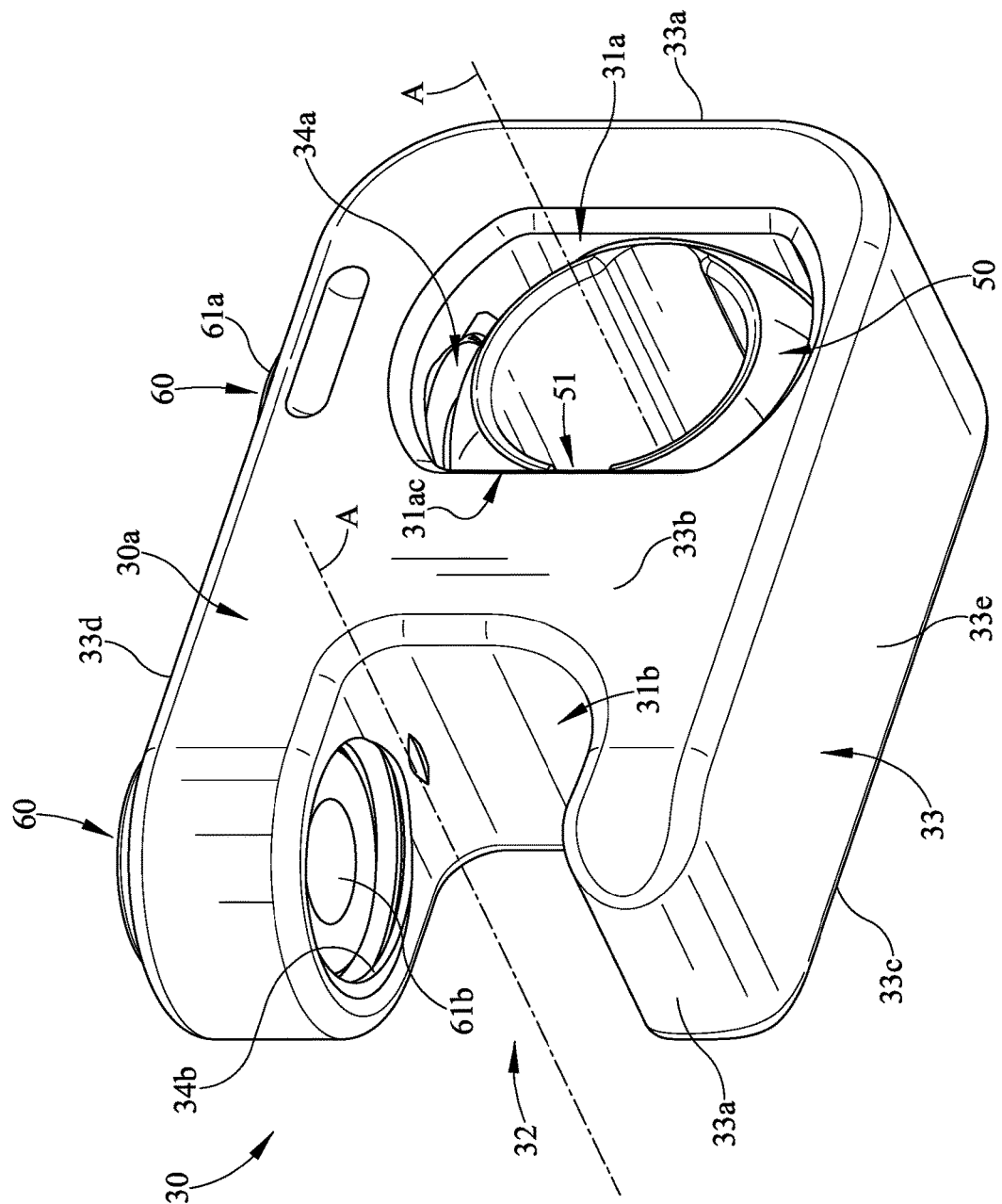
FIG. 3 is a top perspective view of the connector of FIG. 2 illustrating the bushing in the assembled position.
Figure 4:
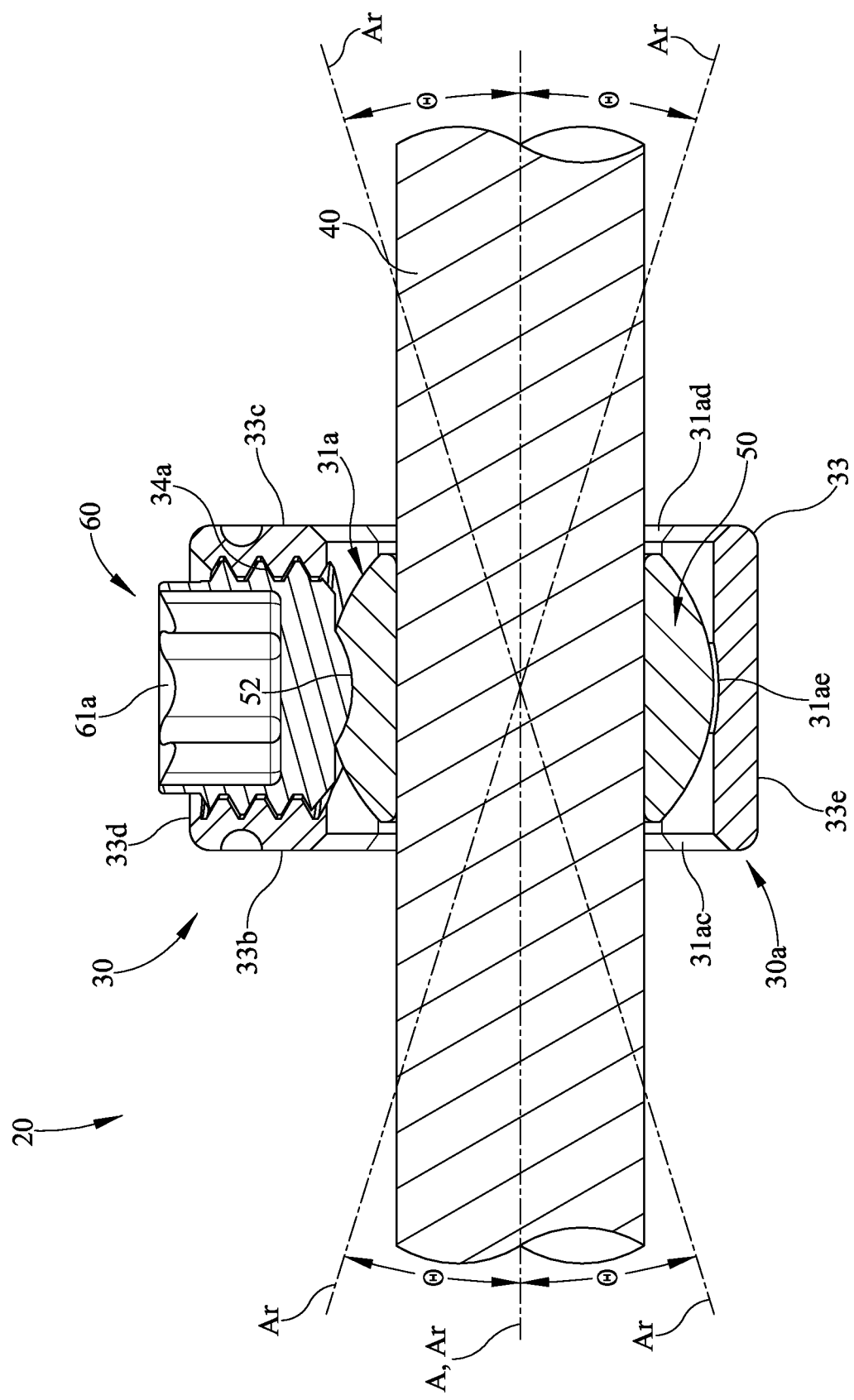
FIG. 4 is a sectional view taken along line 4-4 of FIG. 1.

In some implementations, the one or more bushings 50 within the connector 30 may allow for variation of the orientation or angles θ of the one or more rods 2, 40 in one or more planes and/or one or more directions. In the one embodiment as best shown in FIG. 2, the bushing and/or rod 40 positioned within the bushing 50 may have an angle θ (e.g. up to about 8 degrees of angulation) in one or more planes from the axis of the receptacle or a cone of displacement (e.g. up to about 16 degrees) of the rod's axis Ar about the axis A may be used to vary the orientation of the rod. It should be understood that this cone of displacement or angulation may be, but is not limited to, anywhere from 8 to 30 degrees in all or certain planes of motion along the rods axis Ar in some embodiments. Moreover, for example, the cone of angulation about the axis A may be 40 degrees in some embodiments or applications. The displacement or angle θ of the rod in the application may be secured into position upon compression by the bushing/fastener within the threaded opening. In embodiments when two bushings 50 are used, for example in FIG. 8, the two rods 2, 40 may be a variety of angles θ within each corresponding receptacle/bushing to create a variety of angles between the adjacent/connected rods for a variety of applications. It should be understood that a variety of cones/angles or range of angles may be used to position the rod/bushing in one or more planes and still be within the scope of the invention.

For example, the rod may be able to angle to a first angle/cone in one plane and a second or another angle/cone in another plane, where the first angle/cone may be different from the second angle/cone. (e.g. 30 degrees of cone angulation in the sagittal plane and 10 degrees of cone angulation in the coronal plane).

In some implementations, the connector 130 may include two or more variable connections to the one or more rods. As shown in the one embodiment in FIG. 8, each receptacle 31a, 31b of the connector 130 includes the bushing 50 to receive the corresponding rod 40, 2. This one embodiment shown may receive or load both rods 40, 2 axially into the front side 33b and/or back side 33c. The first receptacle 31a includes the first bushing 50 and the second receptacle 31b includes the second bushing 50. Each rod 40, 2 received by the bushing 50, respectively, may be angled independently of the other rod. However, in some embodiments not shown, the first angle θ of one rod may be dependent on the other or second rod's angle θ.

Figure 9:
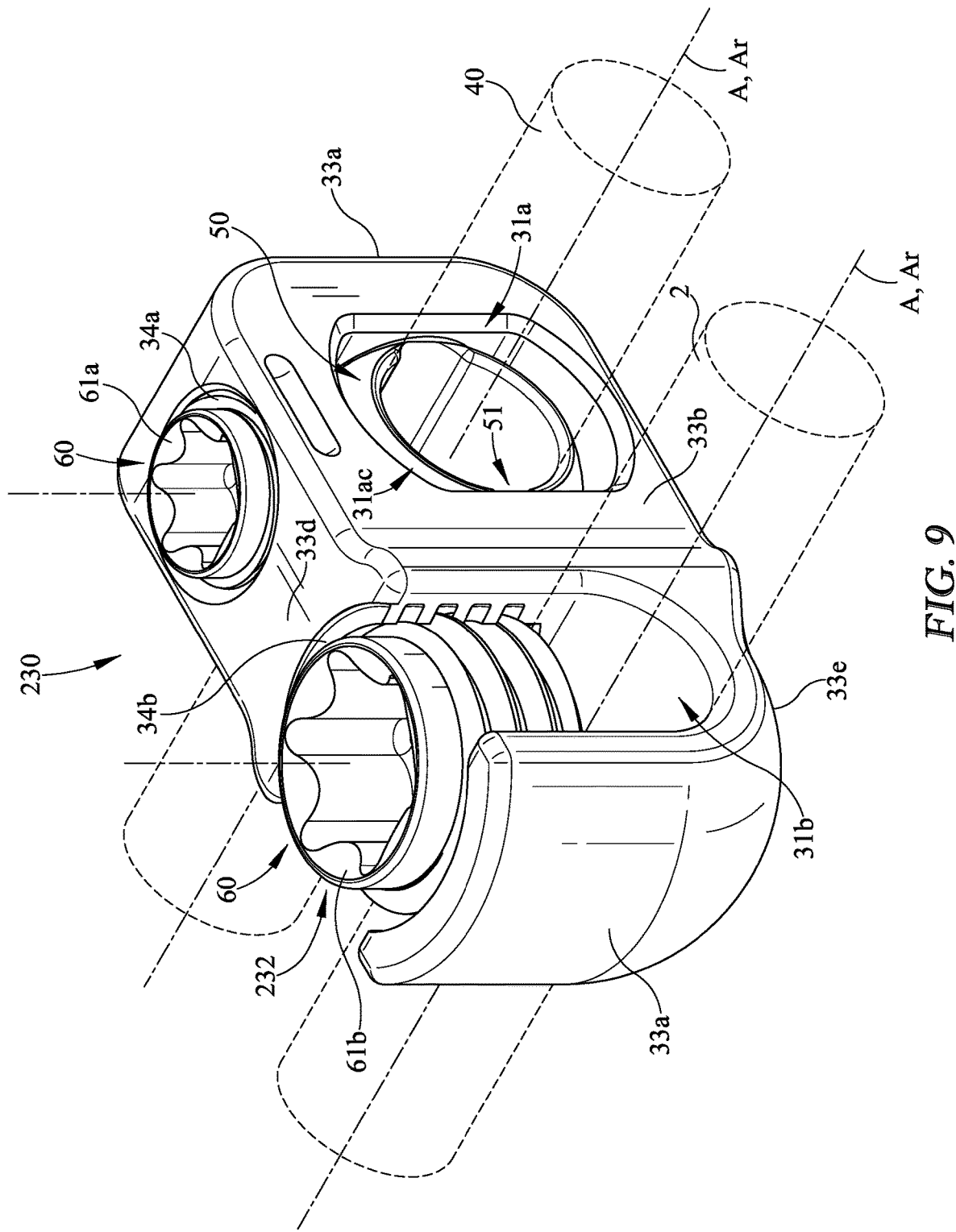
FIG. 9 is a top perspective view of another embodiment of a connector illustrating a top-loading second receptacle.

In some implementations, the connector 230 may include a top-loading receptacle for receiving the rod. As shown in the one embodiment in FIG. 9, the first receptacle 31a may include the bushing 50 and the second receptacle 31b may include a slot 232. The second receptacle 31b may include the receiving slot 232 or be open to engage the rod 2, pedicle screw 3, and/or portions of the pedicle screw system 1. The slot 232 receives the rod 2 (e.g. top-loading). The slot 232 may extend through the outer periphery 33 of the connector 230. The slot 232 may extend through the top side 33d or outer periphery 33 for a depth intersecting with the front side 33b and the back side 33c of the connector 230. As in the one embodiment illustrated in FIG. 9, the slot 232 passes through or may be combined with the second threaded opening 34b to the second receptacle 31b/through opening. The second fastener 61b is threaded into the slot 232 and/or second threaded opening 34b to secure the rod 2 and/or pedicle screw, if used. Although not shown, a pedicle screw 3 or portions thereof may be received or captured within the second receptacle 31b along with the rod 2. For example, the bottom side 33e of the connector 230 may have an opening to the second receptacle 31b to receive the pedicle screw 3. Moreover, the connector 230 may be described as a moveable head to the pedicle screw 3, if used.

In use, the implantable connector system 20 or portions thereof may be implanted into the surgical site or used in a variety of surgical clinical applications. The first rod 40 may be inserted into the first receptacle 31a/first bushing 50 of the first connector 30, 130, 230. The first rod 40 may be axially loaded into the first receptacle 31a of the connector 30, 130, 230. The second rod 2 may be axially-loaded, top loaded, or side-loaded into the second receptacle 31b of the connector 30, 130, 230. In some embodiments, the second receptacle 31b may include the slot 32, 232 within the outer periphery 33 of the connector 30, 230 to engage the rod. Or in some embodiments, a second bushing 50 may be received in the second receptacle 31b of the connector 130 to engage the rod 2. When the rods are inserted into their respective slots 32, 232, bushings 50, and/or receptacles 31a, 31b, the user may thread the fasteners 60 into engagement directly or indirectly (e.g. via the bushing and/or other structure) into contact with the rod. The first rod 40/first bushing 50 may be displaced to a desired angle θ or orientation within the receptacle. The first fastener 61a (e.g. set or locking screw) may be threaded into the engagement with the first bushing 50 compressing the first rod 40 into a fixed position at one or more desired angles θ or orientations. For example, in some embodiments, the rod's axis Ar and/or bushing may be fixedly positioned at an angle θ (e.g. from about zero to about 8 degrees) from the axis A of the receptacle. The second fastener 61b (e.g. set or locking screw) may be threaded into the engagement with the second bushing 50, if used, and/or the second rod 2. If a second bushing 50 is used in the second receptacle 31b, the second rod 2/second bushing 50/remaining portion of the connector may be angled (e.g. angle θ) to a desired orientation. One or more additional or second connectors 30, 130, 230 may be used to connect the first and second rods 2, 40. Moreover, the first and second connectors may be the same or different in a variety of applications. Further, the first and second connectors may be different in shape, size, quantities, and construction (e.g. wider or narrower spacing between receptacles) to accommodate curvature of the one or more connected rods. For example, the axis A of each receptacle may not be parallel to each other in some embodiments. Moreover, the receptacles and/or bushings of one or more connectors may include an inner periphery to accommodate a variety of rod dimensional/construction characteristics (e.g. different diameters). The system 1, 20, in some embodiments, may include one or more pedicle screws attached to the one or more rods and/or connectors. In use, one or more pedicle screws 3 may be implanted into the surgical site. The pedicle screws may include a moveable head to secure to one or more rods. In some embodiments, the connector may include the pedicle screw. In some embodiments, the one or more bushings 50 may be inserted by one or more users into the one or more receptacles 31a, 31b. In various embodiments, the bushing 50 may be axially inserted in the receptacle in the first orientation (e.g. see FIG. 6) different from the final or second orientation(s) (e.g. see FIG. 4) when installed or assembled into the connector/receptacle. Once the bushing is inserted into the receptacle, in some embodiments, the bushing 50 may be pivoted (e.g. 90 degrees) from the first orientation to the second orientation to receive the rod. In some embodiments, the pin 36 may be inserted into the connector to retain the bushing therein.

While several embodiments have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the embodiments described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the teachings is/are used. Those skilled in the art will recognize, or be able to ascertain using no more than routine experimentation, many equivalents to the specific embodiments described herein. It is, therefore, to be understood that the foregoing embodiments are presented by way of example only and that, within the scope of the appended claims and equivalents thereto, embodiments may be practiced otherwise than as specifically described and claimed. Embodiments of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the scope of the present disclosure.

All definitions, as defined and used herein, should be understood to control over dictionary definitions, definitions in documents incorporated by reference, and/or ordinary meanings of the defined terms.

The indefinite articles "a" and "an," as used herein in the specification and in the claims, unless clearly indicated to the contrary, should be understood to mean "at least one."

The phrase "and/or," as used herein in the specification and in the claims, should be understood to mean "either or both" of the elements so conjoined, i.e., elements that are conjunctively present in some cases and disjunctively present in other cases. Multiple elements listed with "and/or" should be construed in the same fashion, i.e., "one or more" of the elements so conjoined. Other elements may optionally be present other than the elements specifically identified by the "and/or" clause, whether related or unrelated to those elements specifically identified. Thus, as a non-limiting example, a reference to "A and/or B", when used in conjunction with open-ended language such as "comprising" can refer, in one embodiment, to A only (optionally including elements other than B); in another embodiment, to B only (optionally including elements other than A); in yet another embodiment, to both A and B (optionally including other elements); etc.

As used in the specification and in the claims, "or" should be understood to have the same meaning as "and/or" as defined above. For example, when separating items in a list, "or" or "and/or" shall be interpreted as being inclusive, i.e., the inclusion of at least one, but also including more than one, of a number or list of elements, and, optionally, additional unlisted items. Only terms clearly indicated to the contrary, such as "only one of" or "exactly one of," or, when used in the claims, "consisting of," will refer to the inclusion of exactly one element of a number or list of elements. In general, the term "or" as used herein shall only be interpreted as indicating exclusive alternatives (i.e. "one or the other but not both") when preceded by terms of exclusivity, such as "either," "one of," "only one of," or "exactly one of." "Consisting essentially of," when used in the claims, shall have its ordinary meaning as used in the field of patent law.

As used herein in the specification and in the claims, the phrase "at least one," in reference to a list of one or more elements, should be understood to mean at least one element selected from any one or more of the elements in the list of elements, but not necessarily including at least one of each and every element specifically listed within the list of elements and not excluding any combinations of elements in the list of elements. This definition also allows that elements may optionally be present other than the elements specifically identified within the list of elements to which the phrase "at least one" refers, whether related or unrelated to those elements specifically identified. Thus, as a non-limiting example, "at least one of A and B" (or, equivalently, "at least one of A or B," or, equivalently "at least one of A and/or B") can refer, in one embodiment, to at least one, optionally including more than one, A, with no B present (and optionally including elements other than B); in another embodiment, to at least one, optionally including more than one, B, with no A present (and optionally including elements other than A); in yet another embodiment, to at least one, optionally including more than one, A, and at least one, optionally including more than one, B (and optionally including other elements); etc.

It should also be understood that, unless clearly indicated to the contrary, in any methods claimed herein that include more than one step or act, the order of the steps or acts of the method is not necessarily limited to the order in which the steps or acts of the method are recited.

In the claims, as well as in the specification above, all transitional phrases such as "comprising," "including," "carrying," "having," "containing," "involving," "holding," "composed of," and the like are to be understood to be open-ended, i.e., to mean including but not limited to. Only the transitional phrases "consisting of" and "consisting essentially of" shall be closed or semi-closed transitional phrases, respectively, as set forth in the United States Patent Office Manual of Patent Examining Procedures, Section 2111.03.

The foregoing description of several embodiments of the invention has been presented for purposes of illustration. It is not intended to be exhaustive or to limit the invention to the precise steps and/or forms disclosed, and obviously many modifications and variations are possible in light of the above teaching. It is intended that the scope of the invention and all equivalents be defined by the claims appended to the application once filed as a non-provisional application.

The invention claimed is:

1. An implantable connector system comprising:
    a connector having a first receptacle, a second receptacle, and a first bushing received in the first receptacle, and wherein the connector includes a first threaded opening intersecting the first receptacle and a second threaded opening intersecting the second receptacle;
    wherein the first receptacle includes a front opening connected to a back opening, a first axis of the first receptacle extending from a front side to a back side of the connector, wherein the front opening includes a continuous closed periphery defined entirely by the front side of the connector and the back opening includes a continuous closed periphery defined entirely by the back side of the connector, wherein the front opening is a slot for a first distance along the first axis of the first receptacle towards the back opening and intersects with an annular groove of the first receptacle formed within the continuous closed periphery defined by the front side of the connector and extending at least partially between and partially spaced from the front opening and the back opening, wherein the first bushing is axially loaded along the first axis through the slot of the first receptacle in a first orientation and when the bushing is positioned proximate the annular groove of the first receptacle the bushing is pivoted to a second orientation different from the first orientation;
    a first rod matingly received within the first bushing when the first bushing is orientated in the second orientation;
    a second rod matingly received within the second receptacle;
    a first fastener configured to threadably engage the first threaded opening; and
    a second fastener configured to threadably engage the second threaded opening.

2. The implantable connector system of claim 1 wherein the connector further includes a second bushing received within the second receptacle, and the second rod is matingly received within the second bushing.

3. The implantable connector system of claim 1 wherein the second receptacle includes a slot extending through an outer periphery of the connector to receive the second rod.

4. The implantable connector system of claim 1 wherein the first fastener and the second fastener are both a set screw.

5. The implantable connector system of claim 1 wherein the first receptacle of the connector includes a through hole and the first bushing includes an indentation, wherein the through hole of the first receptacle and the indentation of the first bushing receives a portion of a pin.

6. The implantable connector system of claim 1 wherein the first bushing is spherical and includes a slot.

7. The implantable connector system of claim 1 further comprising one or more pedicle screws.

8. The implantable connector of claim 1 wherein the first receptacle is slot shaped from the front opening to the back opening.

9. A connector for an implantable connector system, comprising:
 a fixed body defining a first receptacle and a second receptacle;
 the first receptacle, the second receptacle, or both having a bushing therein, wherein the bushing includes a first dimension along a longitudinal axis of a through opening therein and a second dimension perpendicular to the longitudinal axis, and wherein the first dimension is less than the second dimension;
 a first threaded opening intersecting the first receptacle;
 a second threaded opening intersecting the second receptacle;
 a first fastener threadingly engaging the first threaded opening and extending into said first receptacle of the body;
 a second fastener threadingly engaging the second threaded opening and extending into the second receptacle of the body; and
 the first receptacle includes a front opening connected to a back opening of an outer periphery of the fixed body, wherein an axis extends between the front opening and the back opening, wherein at least the front opening is a slot, wherein the slot includes a continuous closed periphery defined only by a front side of the connector and the slot intersects with an annular groove of the first receptacle formed within the continuous closed periphery defined by the front side of the connector and extending at least partially between and partially spaced from the front opening and the back opening, wherein the closed periphery of the slot includes a length dimension and a width dimension perpendicular to and smaller than the length dimension, and wherein the width dimension of the slot is larger than the first dimension of the bushing and smaller than the second dimension of the bushing, wherein the bushing passes through the slot when in a first orientation when inserted into the first receptacle, wherein in the first orientation the width dimension of the slot is aligned with the first dimension of the bushing, and the bushing is pivoted to a second orientation different from the first orientation when assembled with the first receptacle of the fixed body.

10. The connector of claim 9 wherein each one of the first receptacle and the second receptacle includes the bushing.

11. The connector of claim 9 wherein the second receptacle includes a slot extending through an outer periphery of the connector to receive a second rod.

12. The connector of claim 11 wherein the slot passes through the second threaded opening.

13. The connector of claim 9 wherein the first receptacle of the connector includes a through hole and the bushing, wherein the bushing includes an indentation, and wherein the through hole of the first receptacle and the indentation of the bushing receives a portion of a pin.

14. The connector of claim 9 wherein the bushing allows displacement of a rod up to about 8 degrees about an axis of the first receptacle and/or the second receptacle, respectively.

15. A method of implanting an implantable connector system comprising the steps of:
 providing a connector having a first receptacle, a second receptacle, and a first bushing positionable in the first receptacle, the first receptacle includes a front opening in a front side of the connector connected to a back opening in a back side of the connector, wherein an axis extends between the front opening and the back opening, wherein at least the front opening is a slot, wherein the slot includes a continuous closed periphery defined only by the front side of the connector and the slot intersects with an annular groove of the first receptacle formed within the continuous closed periphery defined by the front side of the connector and extending at least partially between and partially spaced from the front opening and the back opening;
 axially loading the first bushing into the first receptacle along the axis in a first orientation;
 pivoting the first bushing to a second orientation different from the first orientation after the first bushing in the first orientation is positioned in the first receptacle, and wherein the first orientation is perpendicular to the second orientation;
 axially loading a first rod into the first bushing along the axis when the first bushing is in the second orientation;
 inserting a second rod into the second receptacle;
 threading a first fastener into a first threaded opening to engage the first bushing; and
 threading a second fastener into a second threaded opening to engage the second receptacle.

16. The method claim 15 wherein the connector includes a second bushing in the second receptacle, and inserting the second rod into the second bushing in the second receptacle.

17. The method of claim 15 further comprising the step of at least one of loading the second rod into the second receptacle by at least axially-loading, top-loading, or side-loading.

18. The method of claim 15 further comprising the step of displacing the first rod and the first bushing up to about 8 degrees from an axis of the first receptacle.

* * * * *